(12) United States Patent
Ivarsson et al.

(10) Patent No.: US 10,098,956 B2
(45) Date of Patent: *Oct. 16, 2018

(54) STABILIZING AGENT FOR PHARMACEUTICAL PROTEINS

(71) Applicant: OCTAPHARMA AG, Lachen (CH)

(72) Inventors: Elsa Ivarsson, Sollentuna (SE); Josefin Knutsson, Vastervik (SE); Brita Rippner, Lidingö (SE); Ulrika Nilsson, Bromma (SE); Irène Agerkvist, Danderyd (SE)

(73) Assignee: OCTAPHARMA AG, Lachen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,922

(22) Filed: May 17, 2016

(65) Prior Publication Data

US 2016/0256555 A1  Sep. 8, 2016

Related U.S. Application Data

(62) Division of application No. 14/245,252, filed on Apr. 4, 2014, which is a division of application No. 13/642,020, filed as application No. PCT/EP2011/056326 on Apr. 20, 2011, now abandoned.

(60) Provisional application No. 61/325,975, filed on Apr. 20, 2010.

(30) Foreign Application Priority Data

Apr. 20, 2010 (EP) .................... 10160470

(51) Int. Cl.
| | |
|---|---|
| A61K 38/48 | (2006.01) |
| A61K 47/26 | (2006.01) |
| A61K 38/19 | (2006.01) |
| A61K 9/19 | (2006.01) |
| A61K 38/37 | (2006.01) |
| A61K 9/00 | (2006.01) |
| C07K 14/535 | (2006.01) |
| C07K 14/755 | (2006.01) |
| C12N 9/64 | (2006.01) |
| C12N 9/96 | (2006.01) |
| C07K 14/745 | (2006.01) |

(52) U.S. Cl.
CPC ............ *A61K 47/26* (2013.01); *A61K 9/0019* (2013.01); *A61K 9/19* (2013.01); *A61K 38/193* (2013.01); *A61K 38/37* (2013.01); *A61K 38/4846* (2013.01); *C07K 14/535* (2013.01); *C07K 14/745* (2013.01); *C07K 14/755* (2013.01); *C12N 9/644* (2013.01); *C12N 9/647* (2013.01); *C12N 9/96* (2013.01); *C12Y 304/21022* (2013.01)

(58) Field of Classification Search
None
See application file for complete search history.

(56) References Cited

U.S. PATENT DOCUMENTS

| 6,518,239 | B1 * | 2/2003 | Kuo | ..................... A61K 9/0075 |
|---|---|---|---|---|
| | | | | 514/21.9 |
| 2005/0013867 | A1 | 1/2005 | Lehrman et al. | |
| 2005/0202072 | A1 | 9/2005 | Buch-Rasmussen et al. | |
| 2008/0090278 | A1 | 4/2008 | Kitabayashi et al. | |
| 2009/0226530 | A1 | 9/2009 | Lassner et al. | |
| 2011/0236412 | A1 | 9/2011 | Drew | |

FOREIGN PATENT DOCUMENTS

| EP | 1 739 179 A1 | 1/2007 |
|---|---|---|
| JP | S62-501562 A | 6/1987 |
| JP | H05508315 A | 11/1993 |
| JP | H-11502833 A | 3/1999 |
| JP | 2006-520366 A | 9/2006 |
| JP | 2007-527892 A | 10/2007 |
| JP | 2008-524338 A | 7/2008 |
| JP | 2009-278980 A | 12/2009 |
| RU | 2370281 C2 | 10/2009 |
| WO | WO-86/04486 A1 | 8/1986 |
| WO | WO-91/18091 A1 | 11/1991 |
| WO | WO-1996/019207 | 6/1996 |
| WO | WO-96/30041 A1 | 10/1996 |
| WO | WO-00/62759 A1 | 10/2000 |
| WO | WO-03/035051 A2 | 5/2003 |
| WO | WO-2003/086443 | 10/2003 |
| WO | WO-2004/082707 A2 | 9/2004 |
| WO | WO-2005/014050 A2 | 2/2005 |
| WO | WO-2005/092928 A1 | 10/2005 |
| WO | WO-2007/019331 A2 | 2/2007 |
| WO | WO-2009/077154 A1 | 6/2009 |
| WO | WO-2009-156430 A1 | 12/2009 |

(Continued)

OTHER PUBLICATIONS

English Translation of Russian Office Action—issued in Application No. 2012149205/15(078966).
Japanese Office Action with English Translation—dated May 26, 2015 (issued in Application No. 2013-505474).
Australian Office Action dated Sep. 1, 2016, in AU2015202570.
International Search Report and Written Opinion dated Apr. 20, 2011, issued in International Application No. PCT/EP2011/056326.
Krenov et al., "Role of the B domain in proteolytic inactivation of activated coagulation factor VIII by activated protein C and activated factor X," Blood Coagulation and Fibrinolysis, vol. 17, No. 5, pp. 379-388 (2006).
WO-2011131720—ISR, Jul. 5, 2011, Octapharma Ag.
WO-2011131720—WO, Apr. 20, 2011, Octapharma Ag.

(Continued)

*Primary Examiner* — Brian Gangle
*Assistant Examiner* — Andrea K McCollum
(74) *Attorney, Agent, or Firm* — Keith G. Haddaway; Kerri M. Patterson; Venable LLP

(57) ABSTRACT

A method for stabilizing a human blood protein or human blood plasma protein with a molecular weight of >10 KDa by adding melezitose to a solution comprising the human blood protein or human blood plasma protein with a molecular weight of >10 KDa.

10 Claims, No Drawings

(56) References Cited

FOREIGN PATENT DOCUMENTS

WO     WO-2010/020690 A1     2/2010
WO     WO-2011131720 A1     4/2011

OTHER PUBLICATIONS

Mollmann S. H. et al., "The stability of insulin in solid formulations containing melezitose and starch, Effects of processing and excipients", Drug Development and Industrial Pharmacy Jul. 2006 (Jul. 2006), PUBMED:16885131, vol. 32, Nr.6, pp. 765-778.

Office Action in Russian Patent Application No. 2012149205/15(078966), dated Apr. 16, 2015.

Office Action issued in Japanese Patent Application No. 2013-505474 dated May 26, 2015.

Wang W, Lyophilisation and development of solid protein pharmaceuticals, Int J Pharm 203, 1-60, 2000.

Carpenter et al., Rational design of stable lyophilized protein formulations: Theory and practice, chapter 5, ed Carpenter and Manning, Kluiwer Academic / Plenum Publishers, New York, 2002.

Bowie et al., Deciphering the Message in Protein Sequences: Tolerance to Amino Acid Substitutions, Science, 1990; 247: 1306-1310.

Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue, J. Cell Biol., 1990; 111:2129-2138.

Lazar et al., Transforming Growth Factor α: Mutation of Aspartic Acid 47 and Leucine 48 Results in Different Biological Activities, Mol. Cell. Biol., 1998; 8:1247-1252.

Bork, Powers and Pitfalls in Sequence Analysis: the 70% Hurdle, Genome Research, 2000; 10: 398-400.

Chang et al., 2002, Practical approaches to protein formulation development in "Rationale Design of stable protein formulations—theory and practice" (J.F. Carpenter and M.C. Manning eds.) Kluwer Academic/Plenum publishers, New York, pp. 1-25.

Office Action with English translation issued in Japanese Patent Application No. 2016-150395, dated Jun. 13, 2017.

Zhong et al., "The N-terminal Epidermal Growth Factor-like Domain in Factor IX and Factor X Represents an Important Recognition Motif for Binding to Tissue Factor," The Journal of Biological Chemistry, vol. 277, No. 5, pp. 3622-3631 (Feb. 1, 2002).

\* cited by examiner

STABILIZING AGENT FOR PHARMACEUTICAL PROTEINS

CROSS-REFERENCES TO RELATED APPLICATIONS

This application is a divisional of U.S. patent application Ser. No. 13/642,020, filed Dec. 27, 2012, published as US 2013/0116410, May 9, 2013, which is a U.S. National Stage of PCT Application No. PCT/EP2011/056326, filed Apr. 20, 2011, published as WO2011/131720, Oct. 27, 2011, which claims the benefit of U.S. Provisional Patent Application No. 61/325,975, filed Apr. 20, 2010, and which claims the benefit of European Patent Application No. 10160470.0, filed Apr. 20, 2010, all of which are hereby incorporated by reference in their entirety.

BACKGROUND OF THE INVENTION

The invention pertains to a method for stabilising a human blood protein or human blood plasma protein with a molecular weight of >10 KDa, a composition in solid or liquid state of human blood protein or human blood plasma protein with a molecular weight of >10 KDa and the use of melezitose for stabilisation of a human blood protein or human blood plasma protein.

The stabilisation of therapeutic proteins is a major challenge for the formulation scientists in the pharmaceutical industry today. There are many kinds of stresses that can cause both reversible and irreversible changes to the proteins, such as aggregation, precipitation or denaturation. These difficulties call for the need of agents that stabilize these delicate proteins. Formulation development is a critical step, requiring careful selection of excipients to provide a high yield of protein activity during the purification process as well as during the pharmaceutical process and as a final product. In particular this is true for human blood proteins and human blood plasma proteins.

One of the most widely used stabilizers for protein formulations are carbohydrates, also called saccharides. Carbohydrates are built of linked basic carbohydrate components called monosaccharides, and can be of different length and can thus have different characteristics.

Sucrose and trehalose, the two most commonly used stabilizers, are both disaccharides, hence composed of two monosaccharides.

As compared to two of the most commonly used carbohydrate stabilizers sucrose and trehalose, which are disaccharides, melezitose is a trisaccharide. It is generally indicated [Wang W, Lyophilisation and development of solid protein pharmaceuticals, Int J Pharm 203, 1-60, 2000; Carpenter J. F., Chang B. S., Garzon-Rodriguez W., Randolph T. W., Rational design of stable lyophilized protein formulations: Theroy and practice, chapter 5, ed Carpenter and Manning, Kluiwer Academic/Plenum Publishers, New York, 2002] that disaccharides are the first choice for stabilisation of proteins both in solution and in lyophilized state. Some disaccharides, such as lactose or maltose, are reducing sugars that can degrade proteins via the Malliard reaction during storage in the solid state. If larger saccharides are used as stabilizers in lyophilized preparations, literature suggests that these are less efficient due to steric hinderance of the protein-stabilizer interaction [Carpenter J. F., Chang B. S., Garzon-Rodriguez W., Randolph T. W., Rational design of stable lyophilized protein formulations: Theroy and practice, chapter 5, ed Carpenter and Manning, Kluiwer Academic/Plenum Publishers, New York, 2002].

The review article Wang, W., International Journal of Pharmaceutics, 203 (2000) 1-60, "Lyophilization and development of solid protein pharmaceuticals", discloses i.a. that maltose, glucose and maltotriose could increase the recovery of catalase activity at 1 mg ml$^{-1}$, but maltopentaose, maltohexaose, and maltoheptaose were not as effective. The ineffectiveness of larger saccharides suggests that protein stabilization by sugars may depend on the glucoside side chain length of the sugar that may interfere with intermolecular hydrogen-bonding between stabilizing sugars and proteins. This review article recommends disaccharides as stabilizers (p. 9/10).

WO-A-2003/086443 discloses the use of carbohydrates including stachyose, melezitose, and various mono- and disaccharides for preparation of intranasally administerable polypeptide preparations. The sugars serve as agents to reduce the effects of shear stress during spraying.

WO-A-86/04486 discloses chromatographic purification of i. a. factor VIII wherein melezitose is used as a hydration additive during the chromatographic process.

WO-A-91/18091 discloses a method of preserving delicate biological substances or organic compounds (a) in a dry state and/or (b) at elevated temperatures and/or (c) under irradiation comprises incorporating in a system containing the said substances or compounds a sugar or a sugar derivative selected from (i) a non reducing glycoside of a polyhydroxy compounds selected from sugar alcohols and other straight chain polyalcohols, or (ii) a non-reducing oligosaccharide selected from raffinose, stachyose and melezitose.

Mollmann, S. H. et al reports in Drug Dev. Ind. Pharm. 2006 July; (6):765-78 about the stability of insulin in solid formulations containing melezitose and starch.

BRIEF SUMMARY OF THE INVENTION

The present invention provides a method for stabilising a human blood protein or human blood plasma protein with a molecular weight of >10 KDa by adding melezitose to a solution comprising the human blood protein or human blood plasma protein with a molecular weight of >10 KDa.

Preferably, the human blood protein or human blood plasma protein has a molecular weight of >10 KDa. More preferably, the molecular weight is in the range of 10 KDa to 300 KDa. Most preferably, the molecular weight is in the range of 20 KDa to 200 KDa. It may be advantageous that the human blood protein or human blood plasma protein has a molecular weight range of 50 KDa to 100 KDa or a molecular weight range of 100 KDa to 150 KDa or a molecular weight range of 150 KDa to 200 KDa.

In particular, the human blood protein or human blood plasma protein with a molecular weight of >10 KDa is a pharmaceutically or biologically relevant protein. The pharmaceutically or biologically relevant human blood protein or human blood plasma protein with a molecular weight of >10 KDa which can be stabilised according to the invention can be a recombinantly produced human blood protein or human blood plasma protein.

The term "protein" includes chemically synthesised proteins as well as naturally synthesised proteins which are encoded by genes of cultivated cell as well as recombinant proteins secreted by cells. Recombinant proteins are those which are encoded by transgenes introduced into the cells by molecular biology techniques. Proteins can be modified by chemical methods or by enzymes in post translatorial processes.

In accordance with the invention, "protein" includes proteins of human in particular those produced by cell-cultures, but also proteins of other sources such as plants, insects, etc., and mutated, artificial, synthetic, fusion or chimeric proteins.

The term "human blood protein or human blood plasma protein with a molecular weight of >10 KDa" includes in particular human blood clotting factors including fibrinogen, fibrin monomer, prothrombin, thrombin, FV, FVa, FX, FXa, FIX, FIXa, FVII, FVIIa, FVIII, FXI, FXIa, FXII, FXIIa, FXIII, FXIIIa, von Willebrand factor, ADAMTS13 etc., transport proteins such as albumin, transferrin, ceruloplasmin, haptoglobin, hemoglobin, hemopexin, etc., protease inhibitors such as β-antithrombin, α-antithrombin, α2-macroglobulin, Cl-inhibitor, tissue factor pathway inhibitor (TFPI), heparin cofactor II, protein C inhibitor (PAI-3), Protein C, Protein S, Protein Z, etc., immunoglobulin's such as polyclonal antibodies (IgG), monoclonal antobodies, IgG1, IgG2, IgG3, IgG4, IgA, IgA1, IgA2, IgM, IgE, IgD, Bence Jones protein etc., cell related plasma proteins such as fibronectin, thromboglobulin, platelet factor4, etc., apolipoproteins such as apo A-I, apo A-II, apo E, complement factors such as Factor B, Factor D, Factor H, Factor I, C3b-Inactivator, properdin, C4-binding protein etc., growth factors like Platelet derived growth factor (PDGF), Epidermal growth factor (EGF), Transforming growth factor alfa (TGF-α), Transforming growth factor beta (TGF-β), Fibroblast growth factor (FGF) and Hepatocyte growth factor, antiangionetic proteins such as latent-antithrombin and prelatent-antithrombin etc., highly glycosylated proteins including alfa-1-acid glycoprotein, antichymotrypsin, inter-α-trypsin inhibitor, α-2-HS glycoprotein, C-reactive protein, and other human blood proteins or human blood plasma proteins with a molecular weight of >10 KDa such as histidine-rich glycoprotein, mannan binding lectin, C4-binding protein, fibronectin, GC-globulin, plasminogen, α-1 microglobulin, C-reactive protein, blood factors such as erythropoeitin, interferon, tumor factors, tPA, gCSF and derivatives and muteins thereof. Particularly of interest is factor IX, factor VIII, G-CSF, vWF, antithrombin (AT), Hepatocyte Growth Factor (HGF), polyclonal IgG, alfa-1 antitrypsin, Factor H, Factor I, C1-esterase inhibitor, Factor VII and combinations thereof. However, polypeptides such as insulin are not covered by the term "Human blood protein or human blood plasma protein with a molecular weight of >10 KDa" simply because insulin has a molecular weight of about 5.700 Da.

The terms "human blood protein" and "human blood plasma protein" include derivatives, especially molecules that have been modified to have an extended half-life. Modifications for half-life prolongation include, but are not limited to, fusion proteins, proteins modified by mutagenesis and proteins linked to a conjugate by covalent or non-covalent binding. According to the invention the human blood plasma proteins or human blood proteins may be covalently coupled to hydroxyl ethyl starch (HES) molecules, in particular providing molecules with a molecular weight of 20 to 200 KDa.

Where reference is made to the molecular weight, this refers to the molecular weight of the compounds (i.e. including the molecular weight of any chemical compound covalently coupled to the protein).

The present invention provides in particular a method wherein the solution is transferred into the solid state.

DETAILED DESCRIPTION OF THE INVENTION

This invention relates to the finding of a new stabilizing agent for a pharmaceutical human blood protein or human blood plasma protein with a molecular weight of >10 KDa.

Surprisingly, it has been found that melezitose can be used as stabilizer for human blood proteins or human blood plasma proteins with a molecular weight of >10 KDa, such as recombinant factor VIII (170 KDa), factor IX (55 kDa) and HESylated G-CSF (120 kDa). It is expected that human blood proteins and human blood plasma proteins of similar molecular weight will have similar stabilization requirements. For example, factor IX is a vitamin k dependent human blood plasma protein and has biochemical similarities with all other vitamin K dependent human blood plasma proteins. The Gla domain is a common structural feature in all these vitamin K-dependent proteins and immediately after the Gla domain, each of the proteins (except prothrombin) has one or more EGF-like domains. The vitamin K-dependent proteins require $Ca^{2+}$ ions to express their physiological function and the calcium binding sites involve at least the Gla domain and the EGF-like domains. Calcium binding enables these proteins to bind to phospholipids/cell membranes and thus express their full biological activities. Seven human blood plasma proteins are known to be dependent on vitamin K for their biosynthesis. They are prothrombin (factor II, 72 KDa), factor VII/factor VIIa (50/50 KDa), factor IX (55 KDa) or factor IXa, factor X (59 KDa) or factor Xa, protein C (62 KDa), protein S (69 KDa) and protein Z (62 KDa).

Surprisingly it has been found that human blood proteins and human blood plasma proteins which are covalently bound with a hydroxylethyl starch (HES) molecule with a molecular weight in the range of 20-200 KDa are suitable for stabilization with Melezitose.

Melezitose has shown an excellent ability to maintain the protein activity in both lyophilized formulations and in solution.

According to the invention the step of transferring the solution into the solid state is lyophilisation upon adding of melezitose. Melezitose may also be used in combination with other sugars, such as trehalose, or sucrose. Melezitose, also spelled melicitose, is a nonreducing trisaccharide sugar that is produced by many plant sap eating insects, including aphids such as *Cinara pilicornis* by an enzyme reaction. The IUPAC name is (2R,3R,4S,5S,6R)-2-[[(2S,3S,4R,5R)-4-hydroxy-2,5-bis(hydroxymethyl)-3-[[(2R,3R,4S,5S,6R)-3,4,5-trihydroxy-6-(hydroxylmethyl)-2-tetrahydropyranyl]oxy]-2-tetrahydrofuranyl]oxy]-6-(hydroxylmethyl)-tetrahydropyran-3,4,5-triol.

Melezitose has a molecular weight of 504.44 g/mol.
The respective structure is represented by the formula:

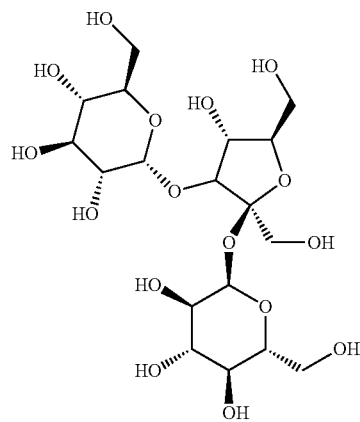 [SMILES: OC[C@H]1O[C@H](O[C@]2(CO)O[C@H](CO)[C@@H](O)C2O[C@H]2O[C@H](CO)[C@@H](O)[C@H](O)[C@H]2O)[C@H](O)[C@@H](O)[C@@H]1O]

Typically melezitose is present in an amount of up to about 1000 mM. The lower limit depends on the amount of melezitose resulting in a sufficient stabilizing effect on the protein of interest. The suitable amount can be readily determined by the skilled person employing the methodology of the examples and his or her general knowledge. A feasible range is for example 10 mM to about 200 mM or from about 10 mM to about 100 mM related to the final formulation.

Preferably the amount larger than 20 mM or larger than 30 mM.

Preferably the amount of melezitose per amount of human blood protein or human blood plasma protein is in the range of 10:1 to 5000:1, preferably in the range of 50:1 to 150:1, or 1000:1 to 3000:1 calculated on a weight per weight basis, i.e. the amount of melezitose is higher than the amount of the protein.

In a preferred embodiment, 10 to 100 mg Melizitose are included in one pharmaceutical dosage of a protein.

Subject of the present invention is a composition comprising a human blood protein or human blood plasma protein with a molecular weight of >10 KDa and melezitose. The composition may be present in the liquid or solid state.

In an embodiment of the invention the composition of the invention is comprising further a bulking agent, a surface active agent, a buffering agent, a further stabilizer and/or tonicity modifier.

A surfactant according to the invention is a compound that adsorbs to surfaces and interfaces and thereby counteracts activity loss of a protein due to adsorption. This type of activity loss may occur during the entire pharmaceutical processing as well as while handling the reconstituted product prior to and during administration to a patient. Commonly used surfactants are Polysorbate 80, Polysorbate 20 and poloxamers, in particular Poloxamer 188. Also proteins such as albumin, in particular recombinant albumin can be used as a surface active agent. Also recombinant albumin may be used according to an embodiment of the invention.

A pH buffering agent is referred to as a compound with a buffering capacity in the optimal pH range of the protein to be formulated. The present invention, when appropriate, embodies sodium citrate, maleic acid, histidine, 2-(4-(2-hydroxy-ethyl)-1-piperazinyl)-ethan sulfonic acid (HEPES), 3-(N-morpholino)propanesulfonic acid (MOPS), 2-(N-morpholino)ethanesulfonic acid (MES), piperazine-N,N'-bis(2-ethanesulfonic acid) (PIPES), or Tris (tris(hydroxymethyl) aminomethane) as a pH buffering agent. The buffering agent is present in an amount to maintain a pH in a range in which the protein stays functional. This is different from one protein to another. The skilled person knows about the preferred ranges of the respective protein, in particular of human blood proteins or human blood plasma proteins with a molecular weight of >10 KDa. As an example, sodium citrate keeps the pH ranging from 6.5 to 7.5. A suitable form of the sodium citrate is the dihydrate form. Generally, the compositions according to the invention can be in lyophilized form, but are also represented by solutions such as a solution to be lyophilized and a solution reconstituted from a lyophilized composition.

A tonicity modifier is referred to as a compound that is present in the formulation to balance tonicity. The present invention, where appropriate, embodies sodium chloride, arginine, glycine, potassium chloride, sugars or sugar alcohols as tonicity modifiers.

Although melezitose exhibits cryo- and lyoprotecting properties, additional cryo- and lyoprotectant (cryo-/lyoprotectant), may also be present. This is a compound present in the formulation to further decrease or prevent loss of protein activity during the freezing and drying steps of a lyophilization process and during subsequent storage of the lyophilized product. The present invention, where appropriate, embodies non-reducing disaccharides such as sucrose and trehalose, and reducing disaccharides, such as maltose and lactose, as additional cryo-/lyoprotectants.

A bulking agent is referred to as an excipient present in the formulation to provide mechanical support to the lyophilized cake and to increase the dry weight. The bulking agent can either be in a crystalline state, as sodium chloride, or in an amorphous state, as arginine. The amount of the bulking agent can be up to 10% by weight based on the final formulation. The present invention, where appropriate, embodies sodium chloride, glycine, mannitol, sucrose or arginine as bulking agent.

A further subject of the present invention is the use of melezitose for long term stabilisation of a protein in the dried state such as lyophilised formulations for at least 6 months, in particular at least 12 months, more particular at least 18 months, still more particular 24 months.

The invention is further described in the following non-limiting examples.

Activity Analysis—Factor VIII

The factor VIII activity was measured with a chromogenic assay or with the one stage assay and the unit of factor VIII was expressed in International Units (IU).

The chromogenic assay is the method prescribed in the European Pharmacopoeia. The method is a two-stage photometric method that measures the biological activity of factor VIII as a cofactor. Factor VIII activates factor X into factor Xa, which in turn is enzymatically cleaved into a product that can be quantified spectrophotometrically.

The one-stage clotting assay is based on the ability of a factor VIII containing sample to correct the coagulation time of factor VIII deficient plasma in the presence of phospholipid, contact activator and calcium ions. The time of appearance of a fibrin clot is measured in one step.

Activity Analysis—Factor IX

The biological activity of factor IX was measured with a one-stage clotting assay and/or a chromogenic assay and the unit of factor IX was expressed in International Units (IU) as defined by the current WHO factor IX concentrate standard.

The one-stage clotting assay is the method prescribed in the European Pharmacopoeia. The principle of the assay is based on the ability of a factor IX containing sample to correct the coagulation time of a factor IX deficient plasma in the presence of phospholipids, contact activator and calcium ions. The time of appearance of a fibrin clot is measured in one step. The factor IX activity is inversely proportional to the coagulation time.

The chromogenic assay is a two-stage photometric method. In the first stage, factor IX is activated to factor IXa by activated factor XI (XIa) in the presence of thrombin, phospholipids an calcium. Factor IXa forms an enzymatic complex with thrombin activated factor VIII (VIIIa) that in the presence of phospholipids and calcium activates factor X into factor Xa. In stage two, factor Xa hydrolyses a factor Xa specific chromogenic substrate thus liberating a chromophoric group pNA that can be quantified spectrophotometrically. The factor IX activity is directly proportional to the amount of generated factor Xa.

Analysis—Recombinant HESylated G-CSF

Resource S HPLC Analysis of HES-G-CSF

The samples are diluted to 0.1 mg/mL with eluent A. 20 μg are injected onto a Resource S 1 mL column (GE Healthcare, Munich, Germany).

Eluent A: 20 mM Na Acetate, pH 4.0
Eluent B: 20 mM Na Acetate, 0.5 M NaCl, pH 4.0
Flow rate: 1 mL/min

| Gradient: | 0%-8% | 1.8-2.0 min |
|---|---|---|
| | 8%-52% | 2.0-13.0 min |
| | 52%-100% | 13.0-13.6 min |

The peak width of the HES-G-CSF peak is taken as quality criterion as it was shown that aggregated HES-G-CSF has a bigger peak width. The gain of peak width is defined as the difference of the HES-G-CSF peak width before and after thermal or shear stress

EXAMPLES

Recombinant Factor VIII

The factor VIII used in the experiments is a recombinant human B-domain deleted factor VIII protein, produced in the human cell line HEK293F according to the process described in EP-A-1 739 179 (Schroder et al). The purification process consisted of five chromatography steps and generated a highly pure factor VIII protein preparation (Winge et al, WO-A-2009/156430) with a human glycosylation like pattern (Sandberg et al, PCT/EP2009/060829).

Plasma Derived Factor IX

The material used in these experiments origins from the commercially available product Nanotiv®, which is a high purity SD treated and nanofiltered factor IX concentrate. Before use in these experiments the material has been further purified over a gel filtration column where the factor IX monomer peak was used for further experiments.

Recombinant HESylated G-CSF

The cell line used is a derivative of human embryonic kidney cell 293 (HEK 293), which was adapted to serum-free growth. This host, HEK 293F, was stably transfected with an expression cassette carrying the cDNA coding sequence for G-CSF. The strong promoter was used for the cassette. The general process is also described in EP 1739179 (Schroder et al).

The purification process consisted of four chromatography steps and generated a highly pure G-CSF protein preparation. The G-CSF protein was coupled to a hydroxylethyl starch (HES) derivative of a molecular weight of approximately 100 KDa. Finally, the HES-G-CSF was purified from the non reacted HES derivative and G-CSF by one chromatography step, resulting in a molecule with a total molecular weight of approximately 120 KDa.

Example 1: Stabilisation of rFVIII by Melezitose in Solution

Preparation

The recombinant factor VIII (rFVIII) was prepared according to the description in the experimental section above. This experiment compared the stabilizing effect of melezitose on rFVIII in solution, with that of the commonly used stabilizer trehalose. The concentration of rFVIII was 100 IU/ml. The compositions of the formulations investigated in this experiment are displayed in Table 1.

TABLE 1

Compositions of the formulation.

| | 1A | 1B |
|---|---|---|
| Melezitose, mM | — | 48 |
| Trehalose dihydrate, mM | 63 | — |
| NaCl, mg/ml | 30 | 30 |
| Calcium chloride dihydrate, mg/ml | 0.5 | 0.5 |
| Poloxamer 188, mg/ml | 2 | 2 |
| Histidine, mg/ml | 3 | 3 |

The formulations were stored for up to 7 days at +25° C. to evaluate the protein activity over time. Samples were taken at regular intervals and analyzed with the chromogenic assay, as described in the experimental section above. The results are summarized in Table 2, as percentage of the initial value.

TABLE 2

Results.

| | | Factor VIII activity over time (days), (% of initial value) | | |
|---|---|---|---|---|
| | | 0 | 1 | 7 |
| 1A | +25° C. | 100 | 86 | 85 |
| 1B | +25° C. | 100 | 82 | 86 |

Conclusions of Example 1

This experiment shows that, surprisingly, melezitose, despite of its lower molar concentration, has a stabilizing effect on rFVIII in solution equal to that of trehalose.

Example 2: Stabilisation of rFVIII by Melezitose in Lyophilized Form

Preparation

The recombinant factor VIII (rFVIII) was prepared according to the description in the experimental section above. This experiment compared the stabilizing effect of melezitose with that of the commonly used stabilizer trehalose, over the freeze-drying process and in lyophilized formulations. The concentration of rFVIII was 100 IU/ml. The compositions of the formulations investigated in this experiment are displayed in Table 3.

TABLE 3

Compositions of the formulations.

| | 2A | 2B |
|---|---|---|
| Trehalose, mM | 63 | — |
| Melezitose, mM | — | 48 |
| NaCl, mg/ml | 30 | 30 |
| Calcium chloride dihydrate, mg/ml | 0.5 | 0.5 |
| Poloxamer 188, mg/ml | 2 | 2 |
| Histidine, mg/ml | 3 | 3 |

1.5 ml aliquots of the solutions were lyophilized in a laboratory scale freeze-drier. The protein recovery over the lyophilisation step was 93% for formulation 2B and 86% for formulation 2A. The lyophilized samples were stored for up to 4 weeks at +25° C. and +40° C. to evaluate the protein activity over time. The samples were reconstituted in 1.5 ml water for injections and analyzed with the chromogenic assay, described in the experimental section above. Results are summarized in Table 4.

TABLE 4

Results

| | | Factor VIII activity over time (weeks), (% of initial value) | | | |
|---|---|---|---|---|---|
| | | 0 | 1 | 2 | 4 |
| 2A | +25° C. | 100 | 97 | 89 | * |
| | +40° C. | 100 | 98 | 90 | 93 |
| 2B | +25° C. | 100 | 117 | 95 | * |
| | +40° C. | 100 | 104 | 97 | 99 |

* no significant change

Conclusions of Example 2

Surprisingly, this experiment shows that melezitose is able to protect rFVIII in lower molar concentration than trehalose over the lyophilisation step, and that it stabilizes rFVIII better than trehalose during storage.

Example 3: Stabilisation of rFVIII by Melezitose in Lyophilized Form

Preparation

The recombinant factor VIII (rFVIII) was prepared according to the description in the experimental section above. This experiment compared the stabilizing effect of melezitose at different concentrations over the freeze-drying process and in lyophilized formulations, and also compared the stabilizing effect with the tetrasaccharide Stachyose. The concentration of rFVIII was 170 IU/ml. The compositions of the formulations investigated in this experiment are displayed in Table 5.

TABLE 5

Compositions of the formulations.

| | 3A | 3B | 3C | 3D |
|---|---|---|---|---|
| Melezitose, mM | 48 | 36 | 24 | — |
| Stachyose, mM | — | — | — | 30 |
| NaCl, mg/ml | 30 | 30 | 30 | 30 |
| Calcium chloride dihydrate, mg/ml | 0.5 | 0.5 | 0.5 | 0.5 |
| Poloxamer 188, mg/ml | 2 | 2 | 2 | 2 |
| Sodium citrate, mg/ml | 2 | 2 | 2 | 2 |

1.5 ml aliquots of the solutions were lyophilized in a laboratory scale freeze-drier. The protein recovery over the lyophilisation step was 91 to 100% for formulations containing melezitose, while the recovery was 84% for formulation 3D containing stachyose as stabilizer. The lyophilized samples were stored for up to 12 months at +25° C. and +40° C. to evaluate the protein activity over time.

The samples were reconstituted in 1.5 ml water for injections and analyzed with the chromogenic assay, described in the experimental section above. Results are summarized in Table 6.

TABLE 6

Results.

| | | Factor VIII activity over time (months), (% of initial value) | | | | | |
|---|---|---|---|---|---|---|---|
| | | 0 | 1 | 2 | 3 | 6 | 12 |
| 3A | 25° C. | 100 | * | n.a. | * | * | 91 |
| | 40° C. | 100 | 96 | 93 | 93 | n.a. | n.a. |
| 3B | 25° C. | 100 | 92 | n.a. | 96 | 95 | 78 |
| | 40° C. | 100 | 90 | 79 | 73 | n.a. | n.a. |
| 3C | 25° C. | 100 | 91 | n.a. | 86 | 86 | 67 |
| | 40° C. | 100 | 70 | 58 | 48 | n.a. | n.a. |
| 3D | 25° C. | 100 | 95 | n.a. | 79 | 65 | n.a. |
| | 40° C. | 100 | 74 | n.a. | 51 | n.a. | n.a. | n.a. = not analysed;
* no significant change

Conclusions of Example 3

This experiment shows that melezitose functions exceptionally well as a stabilizer for rFVIII over the lyphilization step and in lyophilized form. Also, it shows that stachyose is not a preferable stabilizer for lyophilized formulations, as it shows very unsatisfactory results during storage at both 25° C. and at 40° C., compared to the melezitose containing formulations.

Example 4: Stabilisation of Plasma Factor IX by Melezitose in Lyophilized Form

Preparation

The plasma derived factor IX (pFIX) was prepared according to the description in the experimental section above. This experiment investigates the stabilizing effect of melezitose on pFIX. The concentration of pFIX was 100 IU/ml. The composition of the formulation investigated in this experiment is displayed in Table 7.

TABLE 7

Composition of the formulation.

| | 4A |
|---|---|
| Melezitose, mM | 42 |
| NaCl, mg/ml | 30 |
| Polysorbate 80, mg/ml | 0.1 |
| Sodium citrate, mg/ml | 2.35 |

1.5 ml aliquots of the solutions were lyophilized in a laboratory scale freeze-drier. The lyophilized samples were stored for up to 6 months at +5° C., +25° C. and +40° C. to evaluate the protein activity over time. The samples were reconstituted in 1.5 ml water for injections and analyzed with the chromogenic assay, described in the experimental section above.

Results

The protein recovery over the lyophilisation step was about 100%. The results of the stability study are shown in Table 8.

TABLE 8

| | | Factor IX activity over time (months), (% of initial value) | | | |
|---|---|---|---|---|---|
| | | 0 | 1 | 3 | 6 |
| 4A | 5° C. | 100 | 88 | 87 | 85 |
| | 25° C. | 100 | 94 | 89 | 86 |
| | 40° C. | 100 | 93 | 92 | n.a. | n.a. = not analysed;
* no significant change

Conclusions of Example 4

This experiment shows that, surprisingly, melezitose functions well as a stabilizer for factor IX in lyophilized form.

Example 5: Stabilization of HESylated Recombinant G-CSF by Melezitose in Lyophilized Form Preparation The recombinant HESylated G-CSF (rHES-G-CSF) was prepared according to the description in the experimental section above. The experiment compared the stabilizing effect of melezitose on rHES-G-CSF in lyophilized form, with that of the commonly used stabilizer trehalose. The concentration of rHES-G-CSF was 0.3 mg/ml and the compositions of the formulations investigated are displayed in Table 9.

TABLE 9

| Compositions of the formulation. | | |
|---|---|---|
| | 5A | 5B |
| Melezitose, mM | 70 | — |
| Trehalose, mM | — | 70 |
| NaCl, mg/ml | 30 | 30 |
| Polysorbate 20, mg/ml | 0.2 | 0.2 |
| Histidine, mg/ml | 3 | 3 |

1.5 ml aliquots of the solutions were lyophilized in a laboratory scale freeze-drier. The protein recovery was measured after 4 weeks storage at +40° C. by the Resource S method, described in the experimental section above. Results are summarized in Table 10.

TABLE 10

| Results. | | |
|---|---|---|
| | | Gain of peak width (min) after 4 weeks |
| 5A | +40° C. | 0.04 |
| 5B | +40° C. | 0.06 |

Conclusions of Example 5

This experiment shows that melezitose has a stabilizing effect on rHES-G-CSF better than that of the commonly used stabilizer trehalose at equal molar concentration.

Example 6: Stabilisation of Plasma Factor IX by Melezitose Over the Freeze-Drying Step Preparation The plasma derived factor IX (pFIX) was prepared according to the description in the experimental section above. This experiment investigates the stabilizing effect of melezitose on pFIX over the freeze-drying step, compared to the tetrasaccharide stachyose. The concentration of pFIX was 100 IU/ml. The compositions of the formulations investigated in this experiment are displayed in Table 11.

TABLE 11

| Compositions of the formulations. | | |
|---|---|---|
| | 6A | 6B |
| Melezitose, mM | 42 | — |
| Stachyose, mM | — | 30 |
| NaCl, mg/ml | 30 | 30 |
| Polysorbate 80, mg/ml | 0.1 | 0.1 |
| Sodium citrate, mg/ml | 2.35 | 2.35 |

1.5 ml aliquots of the solutions were lyophilized in a laboratory scale freeze-drier. The samples were analyzed with the chromogenic assay, described in the experimental section above, before and after the lyophilization step.

Results

The protein recovery over the lyophilisation step was about 100% for formulation 6A, while the corresponding recovery for formulation 6B was 84%.

Conclusions of Example 6

This experiment shows that, melezitose functions well as a stabilizer for factor IX over the lyophilization step. However, stachyose is not a suitable candidate as stabilizer since a significant activity loss occurs over the freeze-drying step.

The invention claimed is:

1. A method for the preparation of a human blood plasma protein-containing product comprising a human blood plasma protein with a molecular weight of greater than 10 kDa, wherein the human blood plasma protein is selected from the group consisting of Vitamin K-dependent proteins factor VII and factor IX, wherein the method comprises the following steps:
   (a) providing a human blood plasma protein-containing solution;
   (b) adding melezitose to the human blood plasma protein-containing solution of step (a) to a concentration of between 10 mM and 200 mM of melezitose, wherein the amount of melezitose per amount of human factor VII or human factor IX is in the range of 50:1 to 150:1 when calculated on a weight by weight basis;
   (c) lyophilizing the solution of step (b) to prepare a lyophilized human blood plasma protein-containing product; and
   (d) resuspending the lyophilized human blood plasma protein-containing product of step (c) to prepare a resuspended human blood plasma protein-containing solution;
   wherein the human blood plasma protein is recombinantly produced in cell culture or derived from a human source, and
   wherein the human blood plasma protein is stabilized by the melezitose in the human blood plasma protein-containing solution of step (b), in the lyophilized human blood plasma protein-containing product of step (c), and/or in the resuspended human blood plasma protein-containing solution of step (d).

2. The method of claim 1, further comprising at least one surface active agent selected from the group consisting of recombinant albumin, Polysorbate 80, Polysorbate 20, and Poloxamer in the human blood plasma protein-containing solution of step (b), in the lyophilized human blood plasma protein-containing product of step (c), and/or in the resuspended human blood plasma protein-containing solution of step (d).

3. The method of claim 1, further comprising at least one buffering agent selected from the group consisting of histidine, sodium citrate, 2-[4-(2-hydroxyethyl)piperazin-1-yl]ethanesulfonic acid (HEPES), Tris, 3-morpholinopropane-1-sulfonic acid (MOPS), and 1,4-Piperazinediethanesulfonic acid (PIPES) in the human blood plasma protein-containing solution of step (b), in the lyophilized human blood plasma protein-containing product of step (c), and/or in the resuspended human blood plasma protein-containing solution of step (d).

4. The method of claim 1, further comprising at least one further stabilizer selected from the group consisting of sugars, amino acids, polyols, co-factors and combinations thereof; and/or at least one tonicity modifier selected from the group consisting of sodium chloride, arginine, glycine, potassium chloride, sugars and sugar alcohols; and/or at least one bulking agent selected from the group consisting of glycine, mannitol, sodium chloride, arginine and sucrose in the human blood plasma protein-containing solution of step (b), in the lyophilized human blood plasma protein-containing product of step (c), and/or in the resuspended human blood plasma protein-containing solution of step (d).

5. The method of claim 1, wherein the lyophilized human blood plasma protein-containing product of step (c) has improved long-term stability and shelf-life of at least 6 months.

6. The method of claim 1, wherein the melezitose is present in a concentration from about 10 mM to about 100 mM.

7. The method of claim 2, wherein the Poloxamer is Poloxamer 188.

8. The method of claim 5, wherein the lyophilized human plasma protein-containing product of step (c) has improved long-term stability and shelf-life of at least 12 months.

9. The method of claim 5, wherein the lyophilized human blood plasma-containing product of step (c) has improved long-term stability and shelf-life of at least 24 months.

10. The method of claim 5, wherein the lyophilized human blood plasma-containing product of step (c) has improved long-term stability and shelf-life of at least 36 months.

* * * * *